United States Patent [19]
Kumagai et al.

[11] Patent Number: 5,837,674
[45] Date of Patent: Nov. 17, 1998

[54] PHOSPHOPEPTIDES AND METHODS OF TREATING BONE DISEASES

[75] Inventors: Yoshinari Kumagai, Foster City, Calif.; Akira Otaka, Hirakata, Japan

[73] Assignee: Big Bear Bio, Inc., San Mateo, Calif.

[21] Appl. No.: 675,031

[22] Filed: Jul. 3, 1996

[51] Int. Cl.$^6$ ............................ A61K 38/00; A61K 38/04; A01N 57/10; C07K 5/00
[52] U.S. Cl. .................................. 514/7; 514/12; 514/143; 530/324; 530/330; 530/352; 436/86; 436/103
[58] Field of Search ................................... 514/7, 12, 143; 530/324, 352, 330; 436/86, 103

[56] References Cited

U.S. PATENT DOCUMENTS 5,015,628   5/1991   Reynolds .................................... 514/12

FOREIGN PATENT DOCUMENTS

WO 87/07615   12/1987   WIPO .

OTHER PUBLICATIONS

Boskey, A.L. et al., "Concentration–Dependent Effects of Dentin Phosphophoryn in the Regulation of in Vitro Hydroxyapatite Formation and Growth." *Bone and Mineral* (1990) 11:55–65.

Chappard, D., et al.,"Effects of Tiludonate on Bone Loss in Paraplegic Patients." *J. Bone and Mineral Res.* (1995) 10(1):112–118.

Doi, Y., et al., "Effects of Non–Collagenous Proteins on the formation of Apatite in Calcium β–Glycerophosphate Solutions." *Arch. Oral Biol.*, (1992) 37:15–21.

Gennari,C., et al. "Management of Osteoporosis and Paget's Disease: An Appraisal of the Risks and Benefits of Drug Treatment." *Drug. Saf.* (1994) 11(3):179–195.

Glimcher, E.G., et al., "Mechanism of Calcification: Role of Collagen Fibrils and Collagen–Phosphoprotein Complexes in Vitro and in Vivo." *Ant Rec.* (1989) 224:139–153.

Linde, A., et al., "Mineral Induction by Immobilized Proteins." *Calcif. Tissue Int.* (1989) 44:286–295.

Lufkin, E.G., et al., "Pamidronate: An Unrecognized Problem in Gastrointestinal Tolerability." *Osteoporos Int.* (1994) 4(6): 320–322.

Lussi, A., et al., "Induction and Inhibition of Hydroxyapatite Formation by Rat Dentine Phosphoprotein." *Arch Oral Biol.* (1988) 33:685–691.

Nawrot, C.F., et al., "Dental Phosphoprotein–Induced Formation of Hydroxyapatite during in Vitro Synthesis of Amorphous Calcium Phosphate." *Biochemistry* (1976) 51:3445–9.

van den Bos, T. et al., "Effect of Bound Phosphoproteins and Other Organic Phosphoproteins and Other Organic Phosphates on Alkaline Phosphatase–Induced Mineralization of Collagenous Matrices in Virtro." *Bone and Mineral* (1993) 23:81–93.

*Primary Examiner*—Ponnathapura Achutamurthy
*Assistant Examiner*—Padmashri Ponnaluri
*Attorney, Agent, or Firm*—Bozicevic & Reed LLP; Karl Bozicevic

[57] ABSTRACT

Phosphopeptides which significantly reduce bone loss or weakening are provided by the invention. Also provided is a method for treating or preventing any condition associated with bone loss or weakening by administering the phosphopeptides by oral or injectable means.

11 Claims, 4 Drawing Sheets

FIG. 1

Chemical Structure of O-phosphoserine (Pse)

SEQUENCE LISTING ( 1 ) GENERAL INFORMATION:

( i i i ) NUMBER OF SEQUENCES: 3

(2) INFORMATION FOR SEQ ID NO:1:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(D) OTHER INFORMATION: (O- phosphoserine-glycine)3; Xaa=Pse (xi) SEQUENCE DESCRIPTION: SEQ ID NO:1:

Xaa Gly Xaa Gly Xaa Gly
1               5

(2) INFORMATION FOR SEQ ID NO:2:

(i) SEQUENCE CHARACTERISTICS:
(A) LENGTH: 12 amino acids
(B) TYPE: amino acid
(D) TOPOLOGY: linear (ii) MOLECULE TYPE: peptide (ix) FEATURE:
(D) OTHER INFORMATION: (O- phosphoserine-glycine)6; Xaa=Pse (xi) SEQUENCE DESCRIPTION: SEQ ID NO:2:

Xaa Gly Xaa Gly Xaa Gly Xaa Gly Xaa Gly Xaa Gly
1               5                       10

(2) INFORMATION FOR SEQ ID NO:3:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(D) OTHER INFORMATION: (O- phosphoserine-glycine)7; Xaa=Pse (xi) SEQUENCE DESCRIPTION: SEQ ID NO:3:

Xaa Gly Xaa Gly Xaa Gly Xaa Gly Xaa Gly Xaa Gly Xaa Gly
1               5                       10

PHOSPHOPEPTIDES AND METHODS OF TREATING BONE DISEASES

BACKGROUND OF THE INVENTION

1. Technical Field

The invention relates to polypeptides which contain phosphorylated amino acid residues, pharmaceutical compositions which contain such polypeptides and the use of such pharmaceutical compositions for the prevention or treatment of conditions associated with bone loss or weakness.

2. Background Art

It is well-documented that disorders of bone and calcium metabolism cause numerous significant health problems on world-wide basis. For example, in the United States alone, diseases such as osteoporosis, renal osteodystrophy and Paget's Disease afflict over 2 million, 250 thousand, and 50 thousand patients, respectively, and the incidence appears to be increasing.

The majority of bone diseases are characterized by loss of bone minerals (particularly calcium), weakening of bones and consequently, an increase of the frequency and severity of bone fractures. In the elderly population, this has significant social ramifications as well, as many of those with bone fractures have difficultly with mobility, which often leads to the deterioration of other mental and physical functions, resulting in dementia, muscular weakness and/or fatigue. In addition, morbidity and pain are significantly increased by thrombotic events, such as pulmonary embolism which occur as a result of hip or pelvic fractures.

Bone is composed primarily of matrix proteins and calcium salts. Bone growth involves not only an increase in bone size, but an increase in the amount of such components as well. Such material growth of bone provides systemic and local mechanical strength of the skeleton. In the case of bone loss, a significant decline in the contents of these components, rather than in the size of the bone, is more frequently observed. This results in loss of mechanical strength and fractures which occur more frequently and are more severe.

As indicated above, one major function of bone is to provide mechanical strength. In other words, the skeleton needs to be strong enough to support the entire body weight and any additional mechanical burden. Therefore, bone size (mass) and strength must always correlate with whole body weight. Bone growth parallels that of the entire body, with respect to formation and calcium deposition. In humans, the maximum bone mass occurs around the age of 35 and is referred to as "peak bone mass." At peak bone mass, the amounts of matrix protein and calcium are also at their highest, and as a result, mechanical strength is greatest.

It is widely accepted that bone mineral content and density are correlated with the mechanical strength of the bone. After age 35, bone mass and mineral content and accordingly, mechanical strength, begin declining gradually. Consequently, when mechanical strength declines to a certain level, the individual is at greater risk of bone fracture. This natural occurrence is called osteoporosis if severe enough to be pathogenic.

Figure 1:
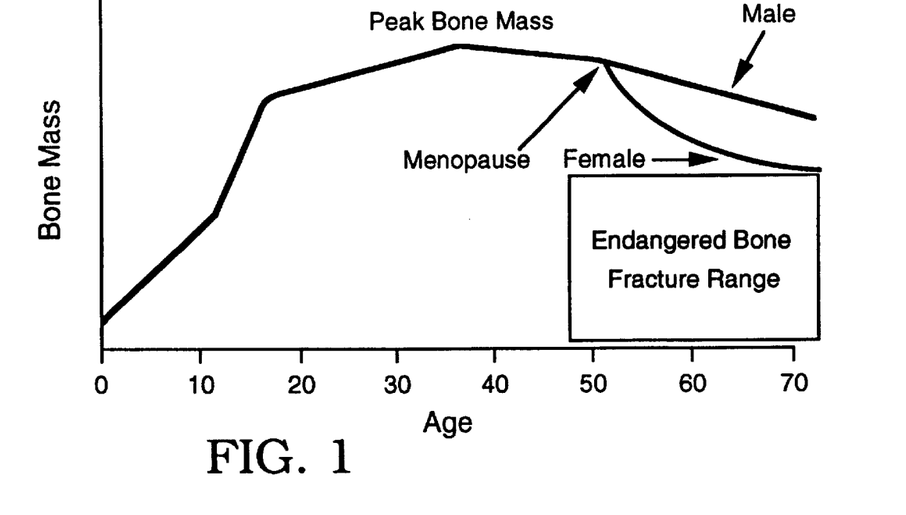
FIG. 1 shows the relationship between bone mass and age.
Figure 2:
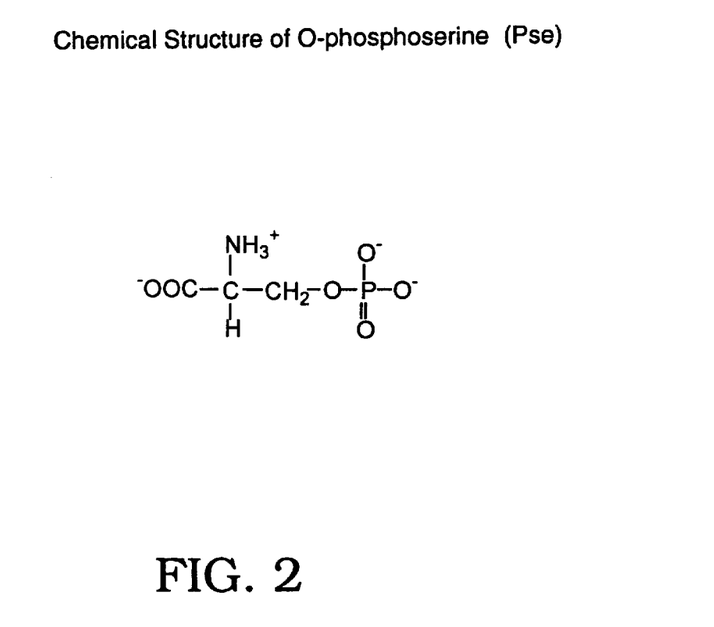
FIG. 2 shows the chemical structure of O-phosphoserine.

The speed at which bone loss occurs differs among individuals, and especially with respect to gender. In females, the speed of bone loss accelerates immediately after menopause (See FIG. 1) because of a significant decline in available estrogen, a hormone which plays a critical role in maintaining healthy bone metabolism. Postmenopausal osteoporosis constitutes an important clinical problem because it afflicts significant numbers of women. Notably, the ratio of female to male osteoporosis patients is 3:1.

Another important function of bone is storage of calcium, an important cation in most biological functions. In mammals, calcium concentration in bodily fluids (such as blood) is kept within a range of 8.5 to 11 mg/dl (2.1 to 2.8 mM). This soluble calcium level is critical in maintaining normal biological functions. Excessive calcium stored in the bone is available for use as needed to maintain adequate levels in bodily fluids. When calcium levels become too low, the body first tries to absorb dietary calcium from the duodenum and intestine, and then if levels are still insufficient, calcium is obtained by dissolving the bone.

Absorption of dietary calcium is stimulated by Vitamin D, synthesized primarily in the kidney. In patients with renal failure who have insufficient intake of dietary calcium, the body must use calcium stored in the bone. This usually causes rapid bone loss and is called renal osteodystrophy (secondary osteoporosis caused by renal failure). Most patients with renal failure are afflicted with this condition regardless of whether they are on dialysis.

Metabolically, bone is a highly active organ with bone degradation (resorption) and reformation (remodeling) occurring continuously. Resorption is facilitated by osteoclasts which are differentiated from monocyte/macrophage lineage cells. Osteoclasts adhere to the surface of bone and degrade bone tissue by secreting acids and enzymes. Osteoblasts facilitate bone remodeling by adhering to degraded bone tissue and secreting bone matrix proteins, which differentiate into bone cells (osteocytes), and become a part of bone tissue. Bone remodeling occurs continuously throughout life.

Numerous experimental approaches have been attempted to either accelerate bone formation or diminish bone resorption. For example, factors such as BMPs (bone morphogenetic proteins), TGF-beta (transforming growth factor), IGF (insulin-like growth factor) are thought to have a significant role in bone formation. However, these factors have not been developed as therapeutic agents for systemic bone diseases. Furthermore, they are not suitable for therapeutic use because they are not available in oral form and cannot be selectively delivered to bone tissue. The fact that the processes of bone formation and resorption are so closely connected makes it extremely difficult to increase or decrease either process.

Type I collagen accounts for the majority of bone matrix proteins and comprises almost 90% of decalcified bone. Type I collagen is composed of three very large (MW>100, 000) protein chains which are mutually cross-linked by hydroxyproline (Hyp) and hydroxylysine (Hyl) residues. Other bone matrix proteins include osteocalcin, Matrix Gla Protein (MGP), Osteonectin, Bone Sialoprotein (BSP), Osteopontin, and Proteoglycans (PG-I and PG-II). These matrix proteins consist of approximately 10% of decalcified bone. Functions of these minor matrix proteins are not completely understood, however, as most of them are acidic proteins, it has been theorized that they may have a role in bone mineralization and/or demineralization.

Osteocalcin (MW=5,930) is composed of 49 amino acid residues which include three Gla (gamma-carboxyl glutamic acid) residues. This protein comprises 1 to 2 % of total bone proteins. It is produced by osteoblast which is stimulated by Vitamin D3. It is an acidic protein and found in demineralization fluid. The function of this protein is thought to be to suppress excessive mineralization (Mikuni-Takagaki et al., *Journal of Bone and Mineral Research* (1995) 10(2) :231–242).

Matrix Gla Protein is composed of 79 amino acids including 5 Gla residues. This protein is usually found in demineralized matrix and believed to have a certain function in the initiation of bone formation.

Osteonectin is a glycoprotein (MW=30,000) which comprises about 20 to 25% of non-collagen matrix proteins in the bone. It has two N-glycosylation sites, and binds Type I collagen and hydroxyapatite. It contains a high ratio of acidic residues such as aspartic and glutamic acid as well as two phosphorylated residues. This protein is thought to be a calcium binding protein and to contribute to acceleration of bone mineralization.

Bone Sialoprotein is a highly glycosylated and sulphated phosphoprotein (MW=57,300). It has two stretches of polyglutamic acid which enable it to bind to hydroxyapatite. Since this protein contains RGD (arginine-glycine-aspartic acid), it has been suggested that it may mediate cell attachment. A number of potential sites for phosphorylation of serine, threonine and tyrosine, O- and N-glycosylation, and tyrosine sulfation are present in this molecule. BSP is expressed in differentiated osteoblasts at bone formation sites and is therefore, theorized to play an important role in bone formation (Shapiro et al., *Matrix* (1993) 13(6):431).

Osteopontin (MW=44,000), is a phosphorylated glycoprotein (sialoprotein) having both N- and O-glycosylation sites, which is found in mineralized bone matrix. It is composed of 301 amino acid residues and 13 of them are phosphorylated residues. Of the phosphorylated residues, 12 are phosphoserine (Pse) and 1 is phosphotyrosine (Pty). It has an RGD which is thought to be recognized by the cells. The exact function of this molecule has yet to be elucidated (Dodds et al., *Journal of Bone and Mineral Research* (1995) 10(11):1666–1680).

Proteoglycan in the bone is PG-I and PG-II and thought to control collagen formation.

In summary, bone matrix is composed of about 90% of Type I collagen and 10% of other minor functional proteins. These proteins (or glycoproteins) are mostly acidic as they contain a number of acidic amino acid residues (aspartic acid, glutamic acid, and gamma-carboxyl glutamic acid). In addition, a few glycosylated phosphoproteins containing number of phosphorylated amino acid residues have been isolated from bone matrix.

There have been a few theories developed regarding the potential role of endogenous phosphoproteins in the mineralization of type I collagen. However, as a relatively small fraction of those phosphoproteins are known to bound to collagenous matrix, the physiological role of the phosphoproteins has remained unclear.

In vitro studies have shown that phosphoproteins trapped in gelatin at very low concentrations promote initiation of the mineralization process (Boskey et al., *Bone and Mineral* (1990) 11:55–65). When in solution, phosphoproteins enhance the conversion of amorphous calcium phosphate into hydroxyapatite (Nawrot et al., *Biochemistry* (1976) 51:3445–3449). At higher concentrations, however, phosphoproteins in solution inhibited the spontaneous precipitation or seeded growth of hydroxyapatite, which is thought to be an important step in matrix mineralization (Termine et al., *Calcified Tissue Research* (1976) 22:149–157; Udich et al., *Biomed. Biochem. Acta.* (1986) 45:701–711; Doi et al., *Arch. Oral Biol.*, (1992) 37:15–21).

It has been shown that immobilized phosphoproteins may promote mineralization of the carrier material to which they are linked. Small amounts of dentinal phosphoproteins or egg yolk phosvitin covalently attached to Sepharose beads have been shown to induce mineral formation in vitro (Lussi et al., *Arch Oral Biol* (1988) 33:685–691; Linde et al., *Calcif. Tissue Int.* (1989) 44:286–295). It was also shown that phosphate groups are important in enhancing the nucleation of a calcium-phosphorus solid phase by collagen-phosphoprotein complexes (Glimcher et al., *Anat Rec* (1989) 224:139–153). In this study, however, the nature of the phosphoprotein-collagen complexes was poorly defined and little information was provided as to the precise experimental conditions that were used.

Another paper reported that phosphoproteins covalently bound to a collagenous matrix promote its mineralization in vitro. This report suggested that the rate of mineralization is influenced by both the amount and the nature of the bound organic phosphate groups. (Van Den Bos et al., *Bone and Mineral* (1993) 23:81–93). In this study, the researchers used only differently phosphorylated rat dentin phosphoproteins as the potential accelerator of bovine bone mineralization and did not speculate as to any specific chemical structures which were responsible for such mineralization. Furthermore, the mineralization assays system used by this group included glycerophosphate which is a commonly used agent in ex vivo bone formation assays. Therefore, it is not clear whether the actual mineralization activity was caused by rat dentin phosphoproteins or glycerophosphate.

All of the theories pertaining to any correlation between collagen mineralization and phosphoproteins have been based upon in vitro experiments. No studies have been conducted using phosphoproteins or phosphopeptides in vivo animal models. This suggests that the current view in the art is that phosphoproteins affect bone mineralization through a specific local phenomenon in the bone.

Currently, there is no effective treatment for bone loss. Therapeutic agents such as estrogen, calcitonin, vitamin D, fluoride, Iprifravon, bisphosphonates, and a few others have failed to provide a satisfactory means of treatment. (Gennari et al., *Drug Saf.* (1994) 11(3):179–95).

Estrogen and its analogues are frequently administered to patients with postmenopausal osteoporosis. Estrogen replacement therapy involves administration of estrogen just prior to or after the onset of menopause. However, as is often the case with steroid hormones, the long term use of estrogen has significant adverse effects such as breast and other gynecological cancers (Schneider et al., *Int. J. Fertil. Menopausal Study* (1995) 40(1):40–53).

Calcitonin, an endogenous hormone produced by the thyroid, binds selectively to osteoclasts, via its receptor, and inactivates them. Since the osteoclast is the only cell which can dissolve bone tissue, calcitonin binding can block or slow down bone degradation caused by the osteoclast. However, this biological mechanism is very short-lived, as the osteoclasts become tolerant to this drug relatively quickly. Therefore, the use of calcitonin does not provide an effective therapeutic option.

Fluoride has been shown to increase bone mass when it is administered to humans. However, while bone mass is increased, mechanical strength is not. Therefore, despite the increase in apparent bone mass, the risk of fracture remains (Fratzl et al., *J. Bone Mineral Res.* (1994) 9(10):1541–1549). In addition, fluoride administration has significant health risks.

Iprifravon has been used to treat osteoporosis in limited areas in the world. However, the actual efficacy of this compound is questionable and it is not widely accepted as a useful therapeutic agent for bone diseases.

Bisphosphonates are compounds derivatized from pyrophosphate. Synthesis involves replacing an oxygen atom situated between two phosphorus atoms with carbon and modifying the carbon with various substituents. While bisphosphonates are known to suppress bone resorption, they have also been shown to inhibit bone formation. Furthermore, bisphosphonates adhere to the bone surface and remain there for very long time causing a long-term decrease in bone tissue turnover. As bone tissue needs to be turned over continuously, this decrease in turnover ultimately results in bone deterioration (Lufkin et al., *Osteoporos. Int.* (1994) 4(6):320–322; Chapparel et al., *J. Bone Miner. Res.* (1995) 10(1):112–118).

Another significant problem with the agents described above is that with the exception of fluoride and iprifravon, they are unsuitable for oral administration, and thus, must be given parenterally. Since bone disorders are often chronic and require long-term therapy, it is important that therapeutic agents be suitable for oral administration.

In summary, a significant need exists for a therapeutic agent which can prevent or treat bone loss, or maintain or increase bone matrix, mineral content, and mechanical strength. A significant need also exists for an efficacious therapeutic agent which can be orally administered, is suitable for long-term use, and is free of significant adverse side-effects. The present inventors have satisfied this need by demonstrating in an in vivo osteoporosis model, that oral or parenteral administration of phosphopeptides significantly reduces bone loss and improves one strength.

SUMMARY OF THE INVENTION

The invention provides phosphopeptides and the use of formulations containing such to treat or prevent any condition associated with bone loss or weakness. The treatment methodology is based on the discovery that oral or parenteral administration of a phosphopeptide prevents bone loss and significantly improved bone strength in an in vivo osteoporosis model.

Thus, in one aspect, the invention is directed to a polypeptide comprising monomer units selected from the group consisting of:

(a) a unit (I) selected from the group consisting of any naturally occurring amino acid and an amino acid residue of the general structural formula (I'):

wherein $R_1$ is any moiety connectable to the carbon atom; and

(b) an amino acid residue of the general structural formula (II):

and $R_2$ is selected from the group consisting of wherein X is and further wherein $R_3$ is an alkyl containing 1 to 7 carbon atoms, which alkyl may be linear, branched, or cyclic, I is not II, and II is present in an amount of at least 10% and the polypeptide comprises from two to thirty monomer units.

In an embodiment of the invention, the polypeptide comprises a unit (I) selected from the group consisting of any naturally occurring amino acid and an amino acid residue of the general structural formula (I'), above, wherein $R_1$ is selected from the group consisting of In another embodiment of the invention, the polypeptide comprises a unit (I) selected from the group consisting of any naturally occurring amino acid and an amino acid residue of the general structural formula (I'):

and (b) (II)

$$^-OOC-\underset{H}{\underset{|}{\overset{NH_3^+}{\overset{|}{C}}}}-CH_2-O-\underset{O}{\underset{\|}{\overset{O^-}{\overset{|}{P}}}}-O^-$$

In another aspect, the invention is directed to a method for the treatment or prevention of any condition associated with bone loss or weakness which comprises administering to a subject in need thereof a compound comprising a chain of naturally occurring amino acids, which chain contains within it a compound of formula (III):

$$\left(-O-\underset{}{\overset{O}{\overset{\|}{C}}}-\underset{H}{\underset{|}{\overset{R_2}{\overset{|}{C}}}}-\underset{}{\overset{H}{\overset{|}{N}}}-\right)_n$$

where $R_2$ is defined above and n is an integer of from 1 to 30 wherein the compound III is preferably administered with a pharmaceutically acceptable carrier and compound III is administered in an amount sufficient to treat or prevent bone loss or weakness.

In still another aspect, the invention is directed to a pharmaceutical composition for treatment or prevention of bone loss or weakness which composition comprises an amount of a polypeptide or compound III as described above sufficient to treat or prevent said bone loss or weakness in admixture with a pharmaceutically acceptable excipient.

MODES OF CARRYING OUT THE INVENTION

Before the present compounds and methods of treatment are described, it is to be understood that this invention is not limited to the particular compounds, methodology or formulations described, as such compounds methods and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a formulation" includes mixtures of different formulations, reference to "an assay" includes one or more assays, and reference to "the method of detection" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated by reference to describe and disclose specific information for which the reference was cited and with which the reference is connected.

The publications discussed herein are provided solely for their disclosure prior to the filing date of the present application. Nothing herein is to be construed as an admission that the invention is not entitled to antedate such publications by virtue of prior invention.

Definitions

The term "treat" is intended to refer to the art of administering medical care, which includes pharmaceutical compositions, to a subject for the purpose of alleviating a pathological condition or for preventing a pathological condition from occurring.

The term "bone loss" refers to any condition in which the bone mass, substance, or matrix or any components of the bone, such as calcium, is decreased or weakened.

The term osteoporosis is intended to refer to any condition involving a reduction in the amount of bone mass or substance resulting from any cause, and in particular, from demineralization of the bone, postmenopausal or perimenopausal estrogen decrease, disease or nerve damage.

The term "subject" refers to any mammal, including a human.

The polypeptides claimed in this invention may be either linear or cyclic peptides, and are comprised of monomer units consisting of a unit (I) selected from the group consisting of any naturally occurring amino acid and an amino acid residue of the general structural formula (I'):

$$^-OOC-\underset{H}{\underset{|}{\overset{NH_3^+}{\overset{|}{C}}}}-R_1$$

wherein $R_1$ is any moiety connectable to the carbon atom; and

(b) an amino acid residue of the general structural formula (II):

$$^-OOC-\underset{H}{\underset{|}{\overset{NH_3^+}{\overset{|}{C}}}}-R_2$$

and $R_2$ is selected from the group consisting of wherein X is and further wherein $R_3$ is an alkyl containing 1 to 7 carbon atoms, which alkyl may be linear, branched, or cyclic, I is not II, II is present in an amount of at least 10% and the polypeptide comprises from two to thirty monomer units. The polypeptide chain may be linear or cyclic.

The amino acids contained in the polypeptide may be either the D- or L- isomer, with naturally occurring L-forms preferred.

In one embodiment, monomer unit (I) is a naturally-occurring amino acid and $R_1$ of monomer unit (I') is defined such that (I') is, alanine, cysteine, aspartic acid, glutamic acid, phenylalanine, glycine, histidine, isoleucine, lysine, leucine, methionine, glutamine, proline, arginine, serine, threonine, valine, tyrosine and tryptophan, asparagine, ornithine, and γ-carboxyl glutamic acid. More preferable $R_1$ defined such that (I') is glycine, alanine or serine, and most preferably, glycine.

In another preferred embodiment, monomer unit (II) is phosphoserine, phosphothreonine or phosphotyrosine, and most preferably phosphoserine.

In another embodiment, number of monomer units contained in the polypeptide consists of at least 2 and less than 30 units, and more preferably 4 to 14 units.

In another embodiment, monomeric unit (II), the phosphorylated amino acid comprises at least 10% of the polypeptide, with 30% being more preferable, and 50% most preferred.

Method of Production

The polypeptides of the invention may be prepared by common peptide synthesis methodologies, generally available in the art. For example, the following method may be used.

The protected dipeptide required for the synthesis of repeated peptides is prepared by solution phase method. Preparations of protected peptides resins are obtained by the DCC-HOBt-mediated coupling of the protected dipeptide on H-Ser(OPO$_3$Me$_2$)-Gly-Merrifield resin which is synthesized by coupling of Boc-Ser(OPO$_3$Me$_2$)-OH on H-Gly-Merrifield resin followed by TFA-mediated Boc deprotection. Crude deprotected peptides are produced by treating the completed protected peptide resins (Boc-(Ser(OPO$_3$Me$_2$)-Gly)n-Merrifield resin, n>1, preferably, n=2–7) with a two-step deprotecting procedure consisting of high acidic (1M TMSOTf-thioanisole in TFA, m-cresol, EDT)- and low acidic (1M TMSOTf-thioanisole in TFA, m-cresol, EDT+additives (TMSOTf+DMS)). Pure peptides are obtained by HPLC purification of crude peptides. The synthesized peptides are then characterized by ion-spray mass spectrometry.

For preparation of longer polypeptides containing more than fourteen amino acids including the phosphorylated ones, a combination of recombinant DNA methodologies and enzymatic or organic synthesis methods may be more suitable.

For example, the polypeptide may be produced by first culturing a cell line transformed with the gene which encodes the amino acid sequence of the basic polypeptide. After producing such a polypeptide by cell culture, the hydroxyl groups of the appropriate amino acid are substituted by phosphate groups using organic synthesis or enzymatic methods with phosphorylation enzymes such as alkaline phosphatase. In the case of serine-specific phosphorylation, more specific enzymes such as serine kinases may be used.

Formulations

The phosphopeptide compounds of the invention are formulated for administration in a manner customary for administration of such materials. Typical formulations are those provided in *Remington's Pharmaceutical Sciences*, latest edition, Mack Publishing Company, Easton, Pa. The percentage of active ingredient in such formulations will be 0.1% to 99% and the percentage of carrier will be 1.0 to 99.9%. The wide range of formulation possibilities are provided in part due to the high degree of solubility of compounds of the type described above. Preferably, the phosphopeptides are administered orally or by injection, including intramuscular, intravenous, subcutaneous or peritoneal injection routes. However, other modes of administration may also be used provided means are available to permit the compounds to enter the systemic circulation, such as transmucosal or transdermal formulations, which can be applied as suppositories, skin patches, or intranasally. In addition, local administration such as by cerebrospinal injection or injection directly into bone or fracture sites may also be used. Any suitable formulation which effects the transfer of the compound to the bloodstream or locally to the bone may properly be used.

For injection, suitable formulations generally comprise aqueous solutions or suspensions using physiological saline, Hank's Solution, or other buffers optionally including stabilizing agents or other minor components. Liposomal preparations and other forms of microemulsions can also be used. The compounds may also be supplied in lyophilized form and reconstituted for administration. Transmucosal and transdermal formulations generally include agents which facilitate transition of the mucosal or dermal barrier, such as bile salts, fusidic acid and its analogs, various detergents, and the like.

For oral administration suitable vehicles are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

The polypeptides of the invention are generally highly water soluble and thus, are easily formulated as an aqueous solution for oral, parenteral or mucosal administration. Solubility increases with the number of phosphorylated residues in a single polypeptide molecule. Water solubility and stability in aqueous solution is often one of the major problems associated with the administration of many peptide drugs. The polypeptides of the invention provide a considerable advantage in this respect.

The nature of the formulation will depend to some extent on the nature of the compound chosen and a suitableformulation is prepared using known techniques and principles of formulation well known to those in the art.

Dosage

The appropriate dosage level will also vary depending on a number of factors including the nature of the subject to be treated (age, sex, weight, etc.), the particular nature of the condition to be treated and its severity, the particular compound used as active ingredient, the mode of administration, the formulation, and the judgment of the practitioner. Generally, dosages will be in the range of 100 µg/kg to 5 mg/kg, preferably 10 mg/kg to 20 mg/kg at a single dosage. Repeated administration may be required according to protocols to be determined considering the variables set forth above. Typically, daily administration over a period of limited period of days may be required or administration by intravenous means may be continuous. For chronic conditions, administration may be continued for longer periods as necessary.

Subjects who would benefit from administration of the polypeptides are those who, for any reason, have bone loss or weakening. Particular, conditions which may be especially amenable to treatment include, but are not limited to, osteoporosis, renal osteodystrophy, osteomalacia, osteodystrophy resolution from other causes, Paget's Disease or osteolysis mediated by cancer, and fractures. Subjects are preferably human, but may include any mammal.

Subjects afflicted with conditions responsive to the method of the invention can readily be identified. In some cases, the nature of the disease itself is diagnostic. Endogenous osteolytic conditions such as osteoporosis, osteomalacia, renal osteodystrophy and Paget's Disease are routinely diagnosed. The presence of osteolysis in general can be verified by ascertaining the presence of bone lesions using x-ray scans. Subjects are preferably human, but may also include any mammal.

Thus, by a variety of criteria, a subject exhibiting the particular syndrome treatable by the method of the invention may be ascertained.

By systemic administration or direct application of the effective dose of the polypeptides, mineral (calcium and phosphorus) and organic matrix content, and the mechanical strength of the bones will be increased. In the case of fracture or breakage, healing will be accelerated.

As shown in Example 1, mineral and organic matrix content and mechanical strength of bone was significantly increased by these polypeptides as demonstrated in an ovariectomized osteoporosis rat model. This effect was observed for both oral and parenteral administration. In one group, low dosage (50 micrograms per animal per day) of a linear peptide of fourteen amino acids including 50% of O-phosphoserine had significant efficacy when administered orally. It was an unexpected discovery that such a large peptide could be administered orally and that it had superior efficacy in bones in vivo. It was also unexpected that mechanical strength of the bones in this group was as high as that of positive control group. Finally, it was unexpected that positive results were obtained with such a low dose of the polypeptide.

During the 90 day treatment period the inventors did not observe any toxicity or other adverse effect or local or systemic health problems. This lack of toxicity or adverse side effect is a significant advantage provided by the polypeptides of the invention, and is especially important for long-term administration necessitated by chronic disorders. In addition, no evidence of calcification or any other histological problem was observed at the subcutaneous injection sites. This is also advantageous because other compounds that increase bone growth can cause calcification or mineralization on the soft tissues. For example, bone morphogenetic proteins cause significant calcification in soft tissues, and thus are suitable only for direct application to the bone.

Mechanism of Action

The mechanism of action of these polypeptides is not completely understood. In other studies, by the inventors, neither the O-phosphoserine-containing polypeptides nor O-phosphoserine monomer had any biological effect on bone in typical in vitro or ex vivo bone formation and resorption assay systems. These results suggests that these polypeptides do not act upon osteoblasts or osteoclasts. These peptides may increase to bone formation by attracting calcium which is solubilized in the biological fluids (serum, bone marrow, and so on, etc.). In addition, these peptides may have an effect on the formation or cross-linking of bone matrix proteins, by forming hydroxyapatite on or between such matrix proteins.

The benefits of the treatment described herein are manifest. In addition to the direct effect of the compounds in reducing bone loss or weakening, any secondary effects of bone loss or weakening may also be addressed. Thus, subjects exhibiting bone loss or weakening may secondarily exhibit hypercalcemia due to the destruction of the bone; the fractured or weakened bones resulting from osteolysis may compress the neural networks in their immediate vicinity ultimately resulting in paralysis or paraplegia; the risk of pathologic fracture is obvious; cachexia can often result; and bone destruction is inevitably associated with pain. All of the foregoing directly or indirectly decrease survival prognosis. Mitigation of these negative effects results from the prevention and treatment of bone loss or weakening.

EXAMPLES

The following examples are put forth so as to provide those of ordinary skill in the art with a complete disclosure and description of how to carry out the method of the invention and utilize the compounds of the invention and are not intended to limit the scope of the invention. Efforts have been made to insure accuracy with respect to numbers used (amounts etc.) but some experimental errors and deviation should be accounted for. Unless indicated otherwise, parts is parts by weight, molecular weight is average molecular weight, temperature is in degrees centigrade and pressure is at or near atmospheric.

Example 1

Prevention of Bone Loss in an Osteoporosis Model Animal Materials and Method:

Ovariectomized rats were chosen for the efficacy study of O-phosphoserine containing polypeptides. Ovaries were surgically resected from young female Harlan-Sprague-Dawley rats. Sham-operated rats were also prepared to use as positive controls.

After 7 days acclimation, the ovariectomized (OVX) rats were randomly divided into different treatment groups (6 animals per each group). Six sham-operated rats were assigned to the positive control group. Each group was fed a normal rat diet throughout the test period but received different treatments as summarized below:

| Group | Rat | Test Sample | Dose per Animal | Adm. Schedule | Route |
|---|---|---|---|---|---|
| 1 | Sham | Saline | 1 ml | Daily | p.o. |
| 2 | OVX | Saline | 1 ml | Daily | p.o. |
| 3 | OVX | Pse | 1000 µg | Daily | p.o. |
| 4 | OVX | (Pse—Gly)$_3$ | 200 µg | Every 3 Days | s.c. |
| 5 | OVX | (Pse—Gly)$_6$ | 200 µg | Every 3 | s.c. |

13
-continued

| Group | Rat | Test Sample Dose per Animal | | Adm. Schedule | Route |
|---|---|---|---|---|---|
| 6 | OVX | (Pse—Gly)₇ | 50 μg | Days Daily | p.o. |

Note:
Sham = sham operated rats
OVX = ovariectomized rats
Pse = O-phosphoserine monomer
p.o. = oral administration
s.c. = subcutaneous injection
(Pse—Gly)₃ = Linear peptide of Pse—Gly—Pse—Gly—Pse—Gly SEQ ID NO:1
(Pse—Gly)₆ = Linear peptide of Pse—Gly—Pse—Gly—Pse—Gly—Pse—Gly—Pse—Gly—Pse—Gly SEQ ID NO:2
(Pse—Gly)₇ = Linear peptide of Pse—Gly—Pse—Gly—Pse—Gly—Pse—Gly—Pse—Gly—Pse—Gly—Pse—Gly SEQ ID NO:3

The test samples four groups 3, 4, 5, and 6 were dissolved in saline and administered at once. Total volume of the sample solution was 1 ml and 0.1 ml per animal for oral and parenteral administration, respectively. Oral preparations were administered once a day and injection (s.c.) was every three days.

For subcutaneous administration, two different injection sites on the back of each animal were alternated. At the end of the study (Day 90), these injection sites were excised and examined histologically to determine whether there was any evidence of calcification.

The group receiving the highest amount of oral Pse (group 3) was used to compare the efficacy of monomeric Pse versus Pse contained in a polypeptide.

On Days 0, 45, and 90 of the treatment, the femurs of most of the participating animals were subject to DEXA (dual energy X-ray absorptiometry) measurement, a typical method by which to study the status of bone growth. The animals were anesthetized and fixed on the bed when receiving the DEXA scan. In addition, after DEXA measurement on Day 90, the animals in the selected groups were euthanized by exsanguination for postmortem examination.

Prior to euthanizing the animals, the subcutaneous injection sites were scored by visual examination for evidence of calcification. Then each subcutaneous injection site and underlying skeletal muscle tissue was collected for histopathology study.

Femurs were collected from the animals and soft tissue was removed. The left femur was subjected to bone composition analysis. First, the isolated femur was mildly dried until all the moisture was eliminated, and dry weight was determined. The femur was then ashed and ash weight was measured. Calcium and phosphorus content in the ash was quantitated by atomic absorptiometry.

The right femur from each animal was subjected to bone mechanical strength measurement (three point bending study). The isolated femur was placed on an apparatus in which two isolated points of the long bone were supported. Weight load was applied at the center of the two supporting points towards the direction in which the bone is bent. The amount of applied load on the bone (in Newton: N) and the degree of deflection of the bent bone from its original position before the load was applied (in mm) was measured. The value of load was plotted against the deflection (load-deflection) curve.

Two points in the initial linear portion of the load-deflection curve were chosen by the operator at the time of testing. A line was constructed through these points, with the slope representing the initial stiffness. The yield point was then calculated as the point where the load predicted by the selected line exceeded the actual load at the same displacement by 5%. The average stiffness was calculated as the slope of the line from the maximum load point to the origin.

Results

Figure 3:
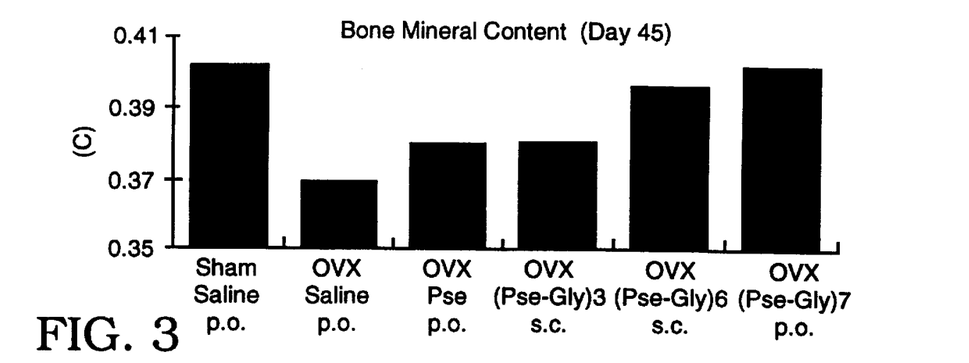
FIG. 3 shows the average bone mineral content of all animals in each group of an osteoporosis animal model, as measured by dual energy x-ray absorptiometry (DEXA) on day 45.
Figure 4:
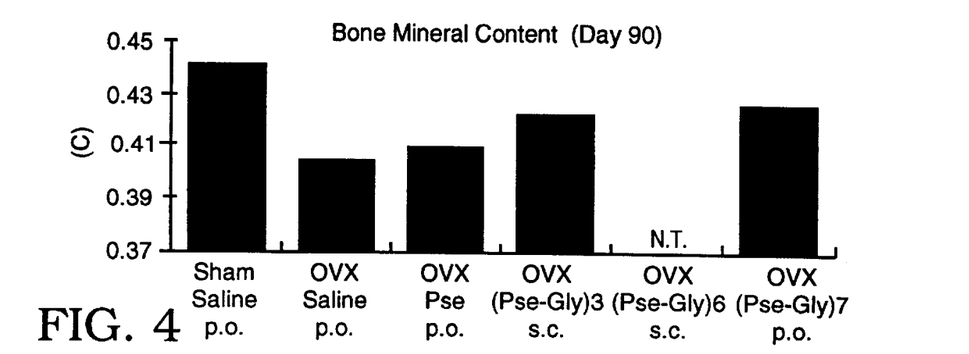
FIG. 4 shows the average bone mineral content of all animals in each group as measured by DEXA on day 90.
Figure 5:
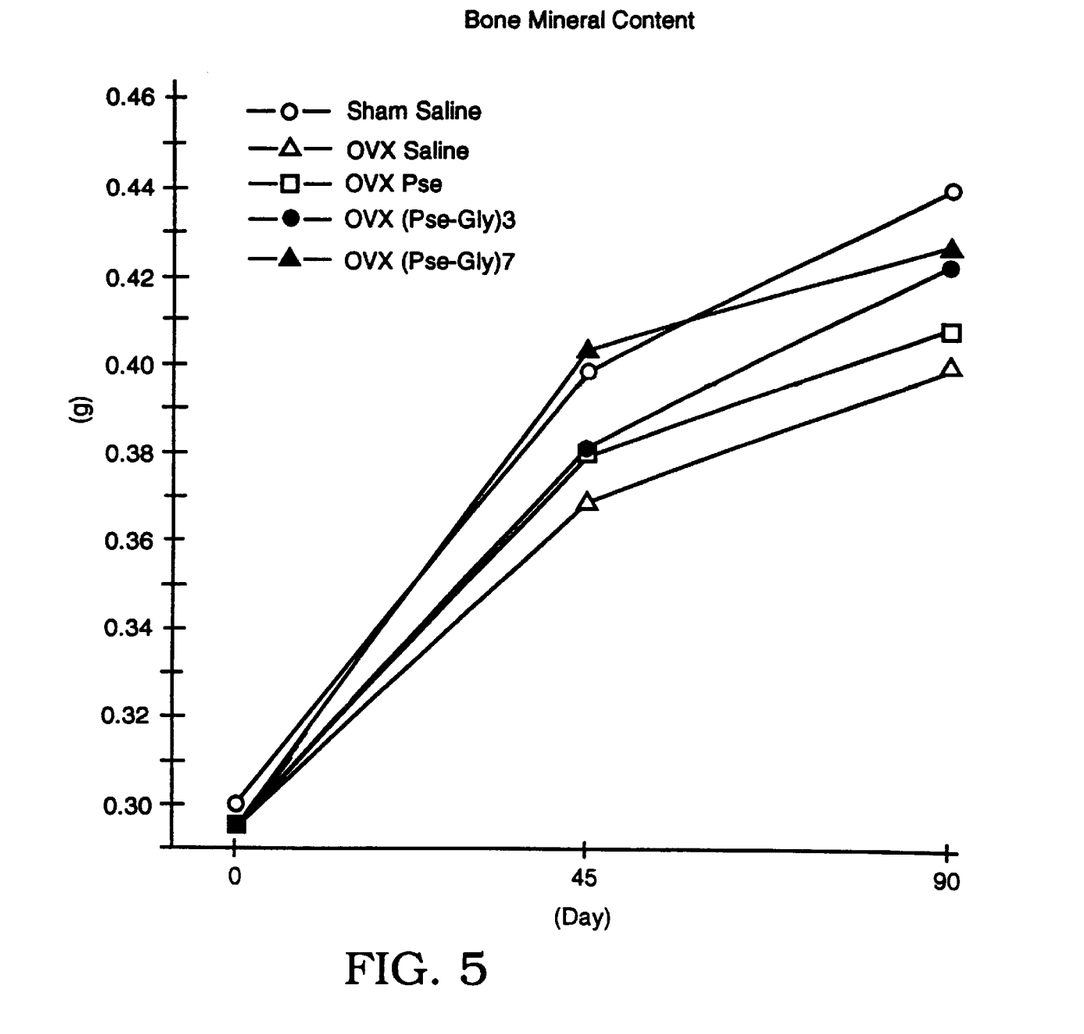
FIG. 5 shows the change in bone mineral content over time in the animals in each group as measured by DEXA on Days 0, 45, 90.

As shown in FIG. 3, on Day 45, the bone mineral content (BMC) measured by DEXA of for groups 3, 4, 5, and 6 fell within the range between that of the positive (group 1) and negative (group 2) control groups. Although the BMC for the monomeric Pse (group 3) and (Pse-Gly)₃(SEQ ID NO:1) (group 4) was close to that of the negative control, BMC for (Pse-Gly)₆(SEQ ID NO:2) (group 5) and (Pse-Gly)₇(SEQ ID NO:3) (group 6) was similar to the positive control. The polypeptide which contained more Pse in a single molecule caused superior bone growth activity. On Day 90 the BMC of (Pse-Gly₃ (SEQ ID NO:1) group (group 4) was the same as that for the longer chain polypeptide (group 6) (See FIG. 4). FIG. 5 shows the change in bone mineral content over a period of time between 0 and 90 days, as measured by DEXA. With the exception of (PSE-Gly)₆(SEQ ID NO:2), all other groups showed an increase over time.

Figure 6:
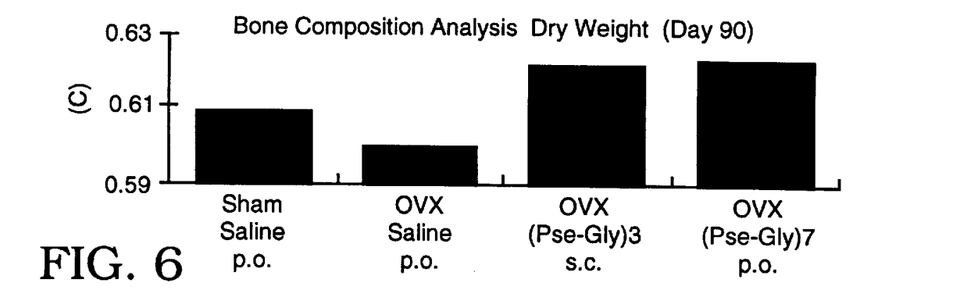
FIG. 6 shows the average dry weight of the right femur of all animals in each group on Day 90.
Figure 7:
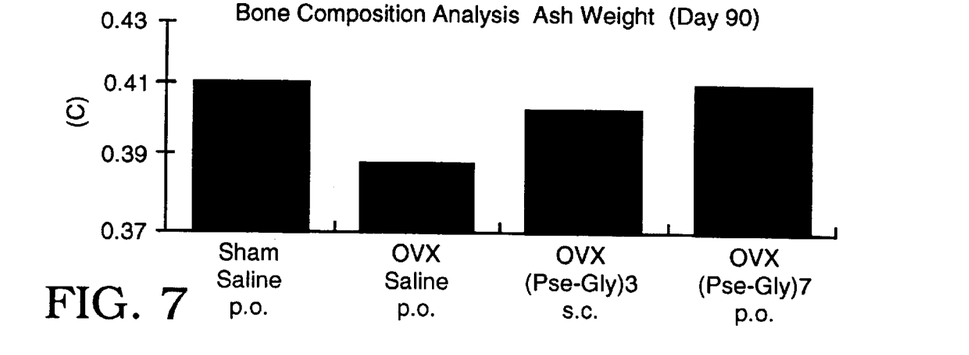
FIG. 7 shows the average ash weight of the right femur of all animals in each group as measured on Day 90.

Groups 1, 2, 4, 6 were selected for the further postmortem examinations. FIGS. 6 and 7 show the dry weight and ash weight, respectively, of the femurs of the animals from each group. Both dry and ash weights of the bones in (Pse-Gly)₃(SEQ ID NO:1) (group 4) and (Pse-Gly)₇(SEQ ID NO:3) (group 6) were significantly higher than those of the negative control (group 2) and similar to, or even higher than, the positive control (group 1). The longer polypeptide with greater Pse was shown to have superior activity in these analyses as well.

Figure 8:
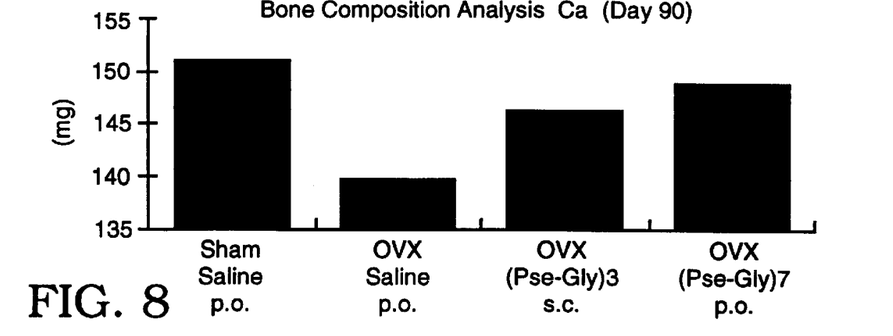
FIG. 8 shows the average calcium content in the femur of all animals in each group as measured on Day 90.
Figure 9:
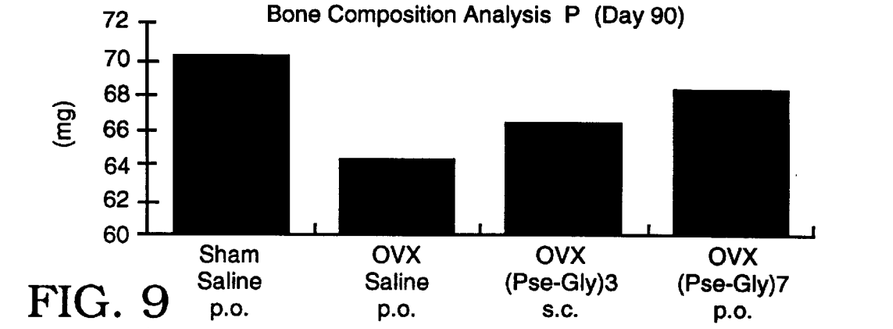
FIG. 9 shows the average phosphorus content in the femur of all animals in each group as measured on Day 90.

FIGS. 8 and 9 show calcium and phosphorus content in the femurs. The results were comparable to data shown in the previous Figures.

Figure 10:
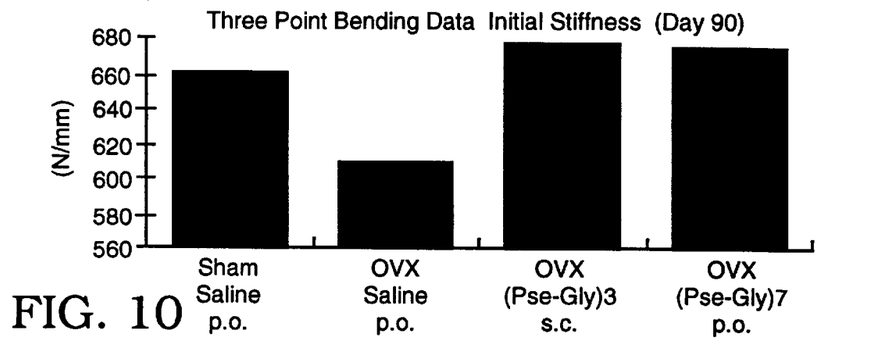
FIG. 10 shows the average initial bone stiffness in the three point bending mechanical strength test of the femur of all animals in each group as measured on Day 90.
Figure 11:
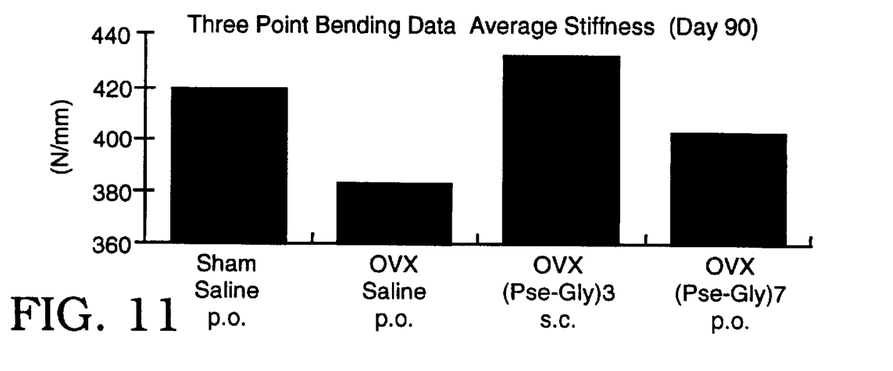
FIG. 11 shows the average value of overall bone stiffness in three point bending mechanical strength test of the femurs of all animals in each group as measured on Day 90.

FIGS. 10 and 11 show bone initial stiffness and overall stiffness, respectively. These data suggest that the mechanical strength of the femurs of both (Pse-Gly)₃(SEQ ID NO:1) and (Pse-Gly)₇(SEQ ID NO:3) groups (groups 4 and 6) were identical to that of the positive control group (group 1).

All animals in the study appeared completely healthy throughout the 90 day experimental period and no complications, toxicity, or other adverse side effects were observed.

The instant invention is shown and described herein in what are considered to be the most practical and preferred embodiments. It is recognized however, that departures may be made therefrom which are within the scope of the invention and that obvious modifications will occur to one skilled in the art upon reading this disclosure.

---

What is claimed is:

1. A non-natural, synthetic polypeptide comprising monomer units selected from the group consisting of:

(a) a unit (I) selected from the group consisting of any naturally occurring amino acid and an amino acid residue of the general structural formula (I'):

$$-OOC-\underset{H}{\overset{NH_3^+}{\underset{|}{C}}}-R_1$$

wherein $R_1$ is selected from the group consisting of D- and L-amino acid side chains, ornithine, and γ-carboxyl glutamic acid; and

(b) an amino acid residue of the general structural formula (II):

$$-OOC-\underset{H}{\overset{NH_3^+}{\underset{|}{C}}}-R_2$$

wherein $R_2$ is selected from the group consisting of

$$-\underset{OX}{\overset{}{\underset{|}{CH}}}-CH_3 \quad -CH_2-\underset{}{\bigcirc}-OX \quad \text{and} \quad -R_3-OX$$

wherein X is wherein $R_3$ is an alkyl containing 1 to 7 carbon atoms, I and II are not the same, and the polypeptide has from two to fourteen monomer units, and I and II are present in alternating positions $(I–II)_n$ where n is an integer of from 1 to 7.

2. The polypeptide of claim 1 wherein $R_1$ is selected from the group consisting of 3. The polypeptide of claim 1 wherein $R_1$ is selected from the group consisting of —H  —CH$_3$  —CHCH$_3$  —CH$_2$CHCH$_3$  and  —CHCH$_2$CH$_3$.
            |              |                    |
           CH$_3$         CH$_3$                CH$_3$

4. The polypeptide of claim 1 wherein $R_1$ is —H.

5. The polypeptide of claim 4 wherein $R_2$ is —CH$_2$OX.

6. A method of treating bone loss comprising administering to a subject in need of such treatment an effective amount of the non-natural, synthetic polypeptide according to claim 1.

7. A pharmaceutical composition which comprises a non-natural, synthetic polypeptide comprising monomer units selected from the group consisting of:

(a) a unit (I) selected from the group consisting of any naturally occurring amino acid and an amino acid residue of the general structural formula (I'):

wherein $R_1$ is selected from the group consisting of D- and L-amino acid side chains, ornithine, and γ-carboxyl glutamic acid; and

(b) an amino acid residue of the general structural formula (II):

wherein $R_2$ is selected from the group consisting of wherein X is and wherein $R_3$ is an alkyl containing 1 to 7 carbon atoms, I and II are not the same, the polypeptide has from two to fourteen monomer units, and I and II are present in alternating positions $(I–II)_n$ where n is an integer of from 1 to 7.

8. The polypeptide of claim 1 wherein said amino acid residue of formula (II) is 9. The polypeptide of claim 1, wherein the amino acid residue of formula (I') is:

10. The polypeptide of claim 8 wherein there are at least four monomer units.

11. The polypeptide of claim 9 wherein there are at least four monomer units.

* * * * *